United States Patent

Hardy

[19]

[11] Patent Number: 6,141,578
[45] Date of Patent: Oct. 31, 2000

[54] METHOD FOR CALCULATING WAVE VELOCITIES IN BLOOD VESSELS

[75] Inventor: Christopher Judson Hardy, Schenectady, N.Y.

[73] Assignee: General Electric Company, Schenectady, N.Y.

[21] Appl. No.: 09/056,801

[22] Filed: Apr. 8, 1998

[51] Int. Cl.[7] ........................................ A61B 5/55
[52] U.S. Cl. ..................... 600/410; 600/419; 324/306; 324/309; 382/128
[58] Field of Search .................... 324/306, 309; 382/128, 130, 131, 132; 600/410, 419

[56] References Cited

U.S. PATENT DOCUMENTS

| 5,150,292 | 9/1992 | Hoffmann et al. | 364/413.07 |
|---|---|---|---|
| 5,309,099 | 5/1994 | Irarrazabal et al. | 324/306 |
| 5,684,398 | 11/1997 | Takiguchi et al. | 324/306 |
| 5,773,975 | 6/1998 | De Becker et al. | 324/306 |
| 5,929,637 | 9/1992 | Taguchi et al. | 324/306 |

OTHER PUBLICATIONS

*Pencil Excitation with Interleaved Fourier Velocity Encoding: NMR Measurement of Aortic Distensibility*, MRM 35:814–819 (1996), Hardy, et al.

*A One–Dimensional Velocity Technique for NMR Measurement of Aortic Distensibility*, MRM 31:513–520 (1994), Hardy, et al.

*Primary Examiner*—Marvin M. Lateef
*Assistant Examiner*—Eleni Mantis Mercader
*Attorney, Agent, or Firm*—Marvin Snyder; Douglas E. Stoner

[57] ABSTRACT

An MRI system produces a series of image frames of a blood vessel using a cardiac gated, M-mode Fourier-velocity-encoding pulse sequence. The pulse-wave velocity of a velocity wave traversing the field of view of the image frames is determined by cross correlating a selected reference image frame with the other image frames to locate the relative position of the velocity wave in each of those other image frames, and calculating the propagation velocity of the velocity wave from its relative positions in those other image frames.

7 Claims, 6 Drawing Sheets

METHOD FOR CALCULATING WAVE VELOCITIES IN BLOOD VESSELS

BACKGROUND OF THE INVENTION

This invention relates to nuclear magnetic resonance imaging methods and systems and, more particularly, to the measurement of a pressure wave along a blood vessel using a magnetic resonance imaging (MRI) system.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated. This signal may be received and processed to form an image.

When utilizing these signals to produce images, magnetic field gradients ($G_x$ $G_y$ and $G_z$) are employed. Typically, the region to be imaged is scanned by a sequence of measurement cycles in which these gradients vary according to the particular localization method being used. The resulting set of received nuclear magnetic resonance (NMR) signals are digitized and processed to reconstruct the image using one of many well known reconstruction techniques.

Aortic stiffness appears to be a correlate of age, fitness, and coronary artery disease. It has been shown to influence left ventricular afterload and is an important variable in the management of ventricular disease. It may also be an early indicator of the presence of atherosclerotic disease as well as a predictor of the likelihood of aneurysmal rupture. A rapid and noninvasive technique for determining aortic distensibility is therefore desirable.

A number of techniques have been proposed for the determination of aortic stiffness, some based on the measurement of variations in aortic diameter and blood pressure over the cardiac cycle and others based on measuring the propagation velocity of a pressure or flow wave along the aorta. One technique described by C. J. Hardy, et al., "A One-Dimensional Velocity Technique for NMR Measurement of Aortic Distensibility", *MRM* 31:513–520 (1994), uses NMR excitation of a cylinder or "pencil" of spins aligned with the aorta to produce M-mode phase-contrast aortic blood-flow images, with cardiac gating and data interleaving employed to increase the effective time resolution. For some patients with weak blood flow or irregular heartbeat, however, this method can produce large measurement uncertainties.

A similar but more robust cardiac gated NMR technique for determining aortic distensibility is disclosed by C. J. Hardy, et al., "Pencil Excitation With Interleaved Fourier Velocity Encoding: NMR Measurement of Aortic Distensibility", *MRM* 35:814–819 (1996). An NMR pencil-excitation pulse is used here also, with a bipolar velocity-encoding gradient followed by a readout gradient applied along the pencil axis. Data interleaving is employed to improve the effective time resolution so that rapid propagation of wavefronts can be followed. In this method, the bipolar gradient is stepped through a range of values, with a Fourier transform applied to produce velocity distribution profiles for different phases of the heart cycle. If a sinusoidal bipolar gradient is employed which has maximum amplitude G and separation between lobe centers of T, then the velocity resolution $V_{res}$ obtained by this method is $$V_{res} = \frac{\pi^2}{2\gamma G T^2} \qquad \text{Eq. 1}$$

where $\gamma$ is the gyromagnetic ratio. The resulting velocity distributions can be produced as a series of image frames in which the velocity wave resulting from the pressure wave can be seen propagating along the aorta. The position of the "foot" of this wave can be measured at successive image frames and used to determine the wave velocity (C). The wave velocity C and the density p of the blood in the vessel can then be used to determine the vessel distensibility D according to the relation $$D = 1/\rho C^2, \qquad \text{Eq. 2}$$

where distensibility is defined as the fractional change in vessel cross-sectional area per unit change in blood pressure. For an incompressible fluid in a stiff vessel, pressure changes are instantaneously transmitted down the vessel, but for a vessel with compliant walls, the pressure wave distends the vessel, and travels along the vessel at a finite velocity.

The measurement of the location of the foot of the velocity wave in each image frame can be both tedious and subjective. An automated method is needed for calculating wave-velocity accurately from a series of image frames.

SUMMARY OF THE INVENTION

A method for acquiring a series of image frames which depict the movement of a velocity wave along a blood vessel and which analyzes those image frames to calculate the pulse-wave velocity of the velocity wave is performed by acquiring a series of image frames which depict wave position along a blood vessel at a succession of time intervals during a cardiac cycle, selecting one of the image frames as a reference image, cross correlating the reference image with others of the image frames to determine the relative position of a feature therein, and calculating velocity of the feature from the determined relative positions.

The wave velocity in a blood vessel is automatically calculated from a series of image frames. The cross correlation of each image frame with the selected reference image frame locates the feature in each image frame relative to the reference frame position. If the most significant moving feature in the image frames is the velocity wave, the relative location of the velocity wave is thus measured. Since the time interval between image frames is known, the velocity at which the feature is moving can be calculated from the slope of a line best fitted to a plot of these relative positions versus time.

DESCRIPTION OF THE PREFERRED EMBODIMENTS

Figure 1:
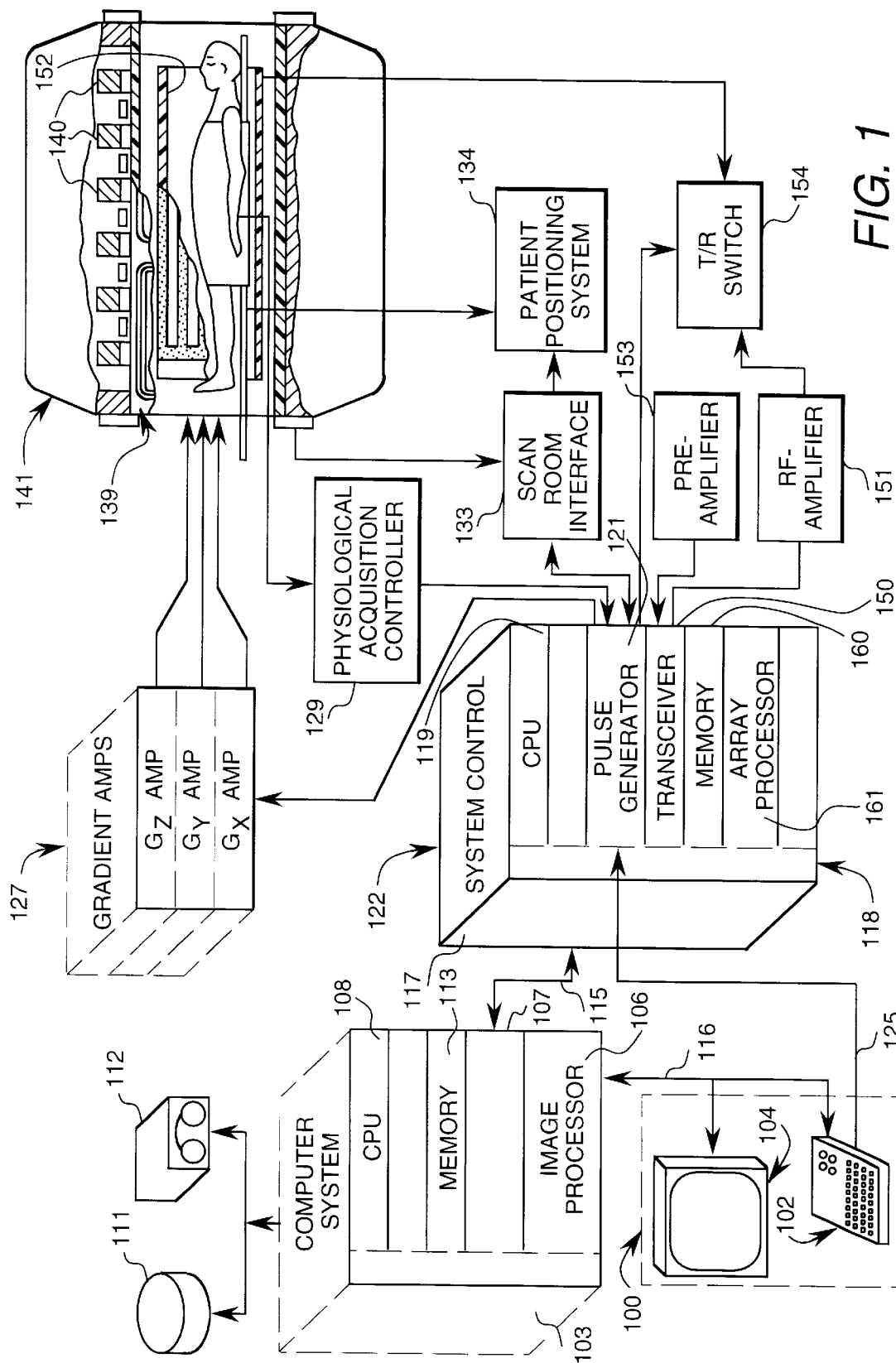
FIG. 1 is a block diagram of an MRI system employing the present invention.

FIG. 1 illustrates the major components of a preferred MRI system incorporating the present invention. Operation of the system is controlled from an operator console 100 which includes a keyboard and control panel 102 and a display 104. Console 100 communicates through a link 116 with a separate computer system 107 that enables an operator to control the production and display of images on the screen 104. Computer system 107 includes a number of modules which communicate with each other through a backplane 103. These modules include an image processor 106, a central processing unit (CPU) 108 and a memory 113 known in the art as a frame buffer for storing image data arrays. Computer system 107 is linked to a disk storage 111 and a tape drive 112 for storing image data and programs, and communicates with a separate system control 122 through a high speed serial link 115.

System control 122 includes a set of modules connected together by a backplane 117. These modules include a CPU 119 and a pulse generator 121 which is coupled to operator console 100 through a serial link 125. Through link 125, system control 122 receives commands from the operator which indicate the scan sequence to be performed. Pulse generator module 121 operates the system components to carry out the desired scan sequence and produces data indicating the timing, strength and shape of the radio frequency (RF) pulses which are to be produced, and the timing and length of the data acquisition interval or window. Pulse generator module 121 is coupled to a set of gradient amplifiers 127, to indicate the timing and shape of the gradient pulses to be produced during the scan. Pulse generator module 121 receives patient data from a physiological acquisition controller 129 that receives signals from a number of different sensors attached to the patient, such as electrocardiograph (ECG) signals from electrodes or respiratory signals from a bellows. Pulse generator module 121 is also coupled to a scan room interface circuit 133 which receives signals from various sensors associated with the condition of the patient and the MR magnet system. Through the scan room interface circuit 133, a patient positioning system 134 receives commands to move the patient to the desired position for the scan.

The gradient waveforms produced by pulse generator module 121 are applied to gradient amplifier system 127 comprised of $G_x$, $G_y$ and $G_z$ amplifiers. Each gradient amplifier excites a corresponding gradient coil in an assembly 139 to produce the magnetic field gradients used for position encoding acquired signals. Gradient coil assembly 139 forms part of a magnet assembly 141 which includes a polarizing magnet 140 and a whole-body RF coil 152. A transceiver module 150 in system control 122 produces pulses that are amplified by an RF amplifier 151 and applied to RF coil 152 through a transmit/receive switch 154. The resulting signals radiated by excited nuclei in the patient may be sensed by the same RF coil 152 and supplied through transmit/receive switch 154 to a preamplifier 153. The amplified NMR signals are demodulated, filtered, and digitized in the receiver section of transceiver 150. Transmit/receive switch 154 is controlled by signals from pulse generator module 121 to electrically connect coil 152 to RF amplifier 151 during the transmit mode and to preamplifier 153 during the receive mode. Transmit/receive switch 154 also enables a separate RF coil (not shown) such as, for example, a head coil or surface coil, to be used in either the transmit or receive mode.

The NMR signals picked up by RF coil 152 are digitized by transceiver module 150 and transferred to a memory module 160 in system control 122. When the scan is completed and an entire array of data has been acquired in memory module 160, an array processor module 161 operates to Fourier transform the data into an array of image data. This array of image data is conveyed through serial link 115 to computer system 107 where it is stored in disk memory 111. In response to commands received from operator console 100, this array of image data may be archived on tape drive 112, or may be further processed by image processor 106 and conveyed to operator console 100 for presentation on display 104.

For a more detailed description of transceiver 150, reference may be made to U.S. Pat. Nos. 4,952,877 and 4,992,736, assigned to the instant assignee.

Figure 2:
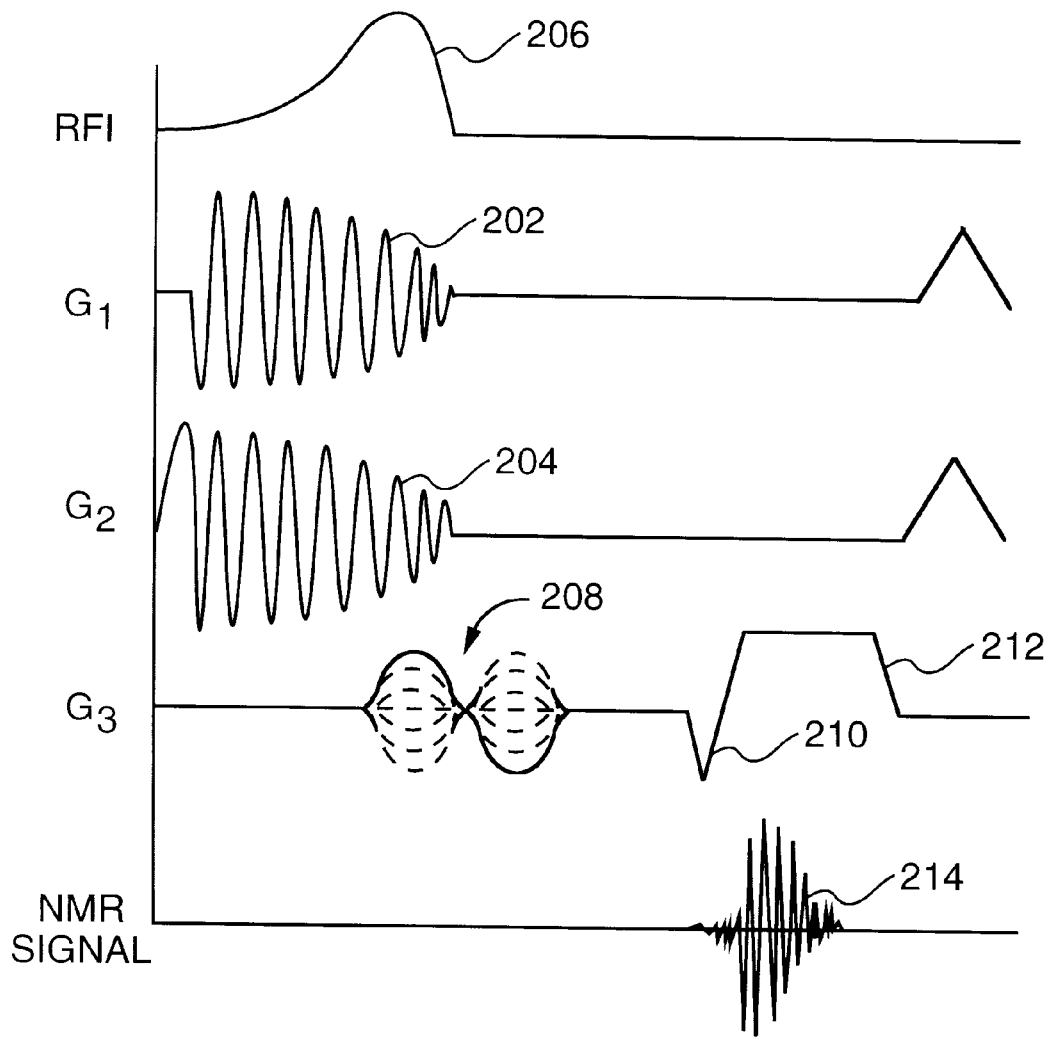
FIG. 2 is a graphic representation of the preferred pulse sequence used to practice the invention.
Figure 3:
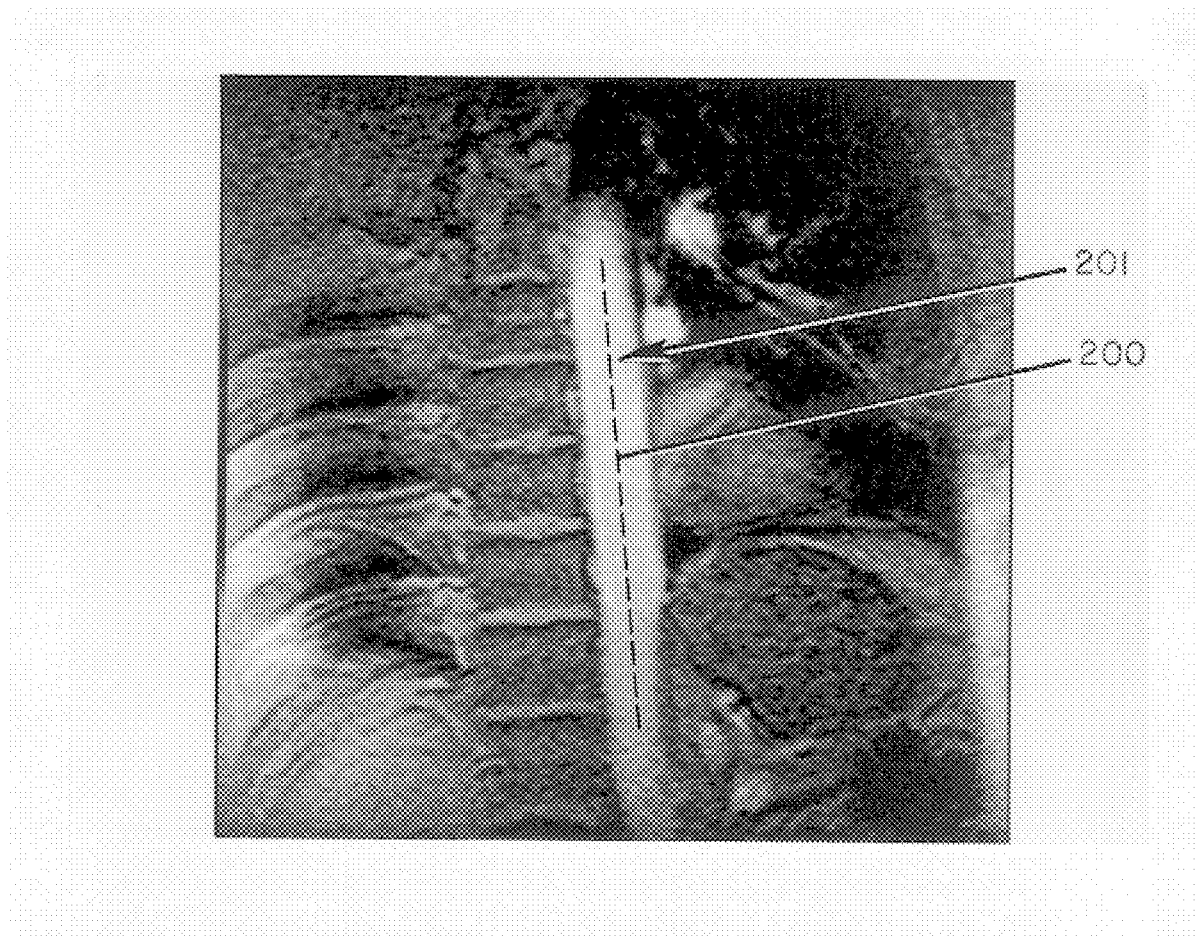
FIG. 3 is a pictorial representation of the region in a blood vessel from which NMR data are acquired with the pulse sequence of FIG. 2.

In practicing the invention, and with reference to FIGS. 2 and 3, a velocity encoded pulse sequence is used to acquire NMR data from a blood vessel. In the example shown in FIG. 3, NMR data are acquired from a cylindrical volume 201 that is 1.5 to 3.0 cm in diameter and from 24 to 32 cm long, aligned along a longitudinal axis 200. A scout scan is performed first to locate the target blood vessel (e.g., the descending aorta) and axis 200 is aligned in the center of the blood vessel. The cylindrical volume 201 of the aorta is excited using a so-called two-dimensional selective excitation. In contrast to the well-known one-dimensional, slice selective excitation which employs a constant magnetic field gradient during application of the RF excitation pulse, two-dimensional selective excitation is achieved by applying, as shown in FIG. 2, two orthogonal, time-varying magnetic field gradients 202 and 204 concurrently with the RF excitation pulse 206. As described in U.S. Pat. No. 4,812,760 entitled "Multi-Dimensional Selective NMR Excitation With A Single RF Pulse" and assigned to the instant assignee, the time variations in the two orthogonal gradients 202 and 204 and the amplitude envelope of the concurrent RF excitation pulse 206 can be chosen to produce the cylindrical volume of excited spins located along axis 200 of FIG. 3. These two gradients 202 and 204, designated $G_1$ and $G_2$ respectively, are orthogonal to axis 200, and vary sinusoidally and diminish to zero during application of RF excitation pulse 206.

A third gradient $G_3$ aligned with axis 200 serves as both a readout gradient and a velocity encoding gradient. This gradient includes a bipolar, velocity encoding gradient 208, followed by a dephasing lobe 210 and a readout gradient pulse 212. An NMR signal 214 is acquired during readout pulse 212 and digitized as described above.

NMR data are acquired using the pulse sequence of FIG. 2 at a succession of times, or phases, during the cardiac cycle to monitor or "see" the effects on the target blood vessel as the blood pressure changes. The repetition rate ($T_r$) of the pulse sequence is 24 ms and is repeated 16 times during each cardiac cycle. To improve the temporal resolution and to velocity encode at a plurality of values, acquisitions are made over a number of cardiac cycles, as described in detail below.

Figure 4:
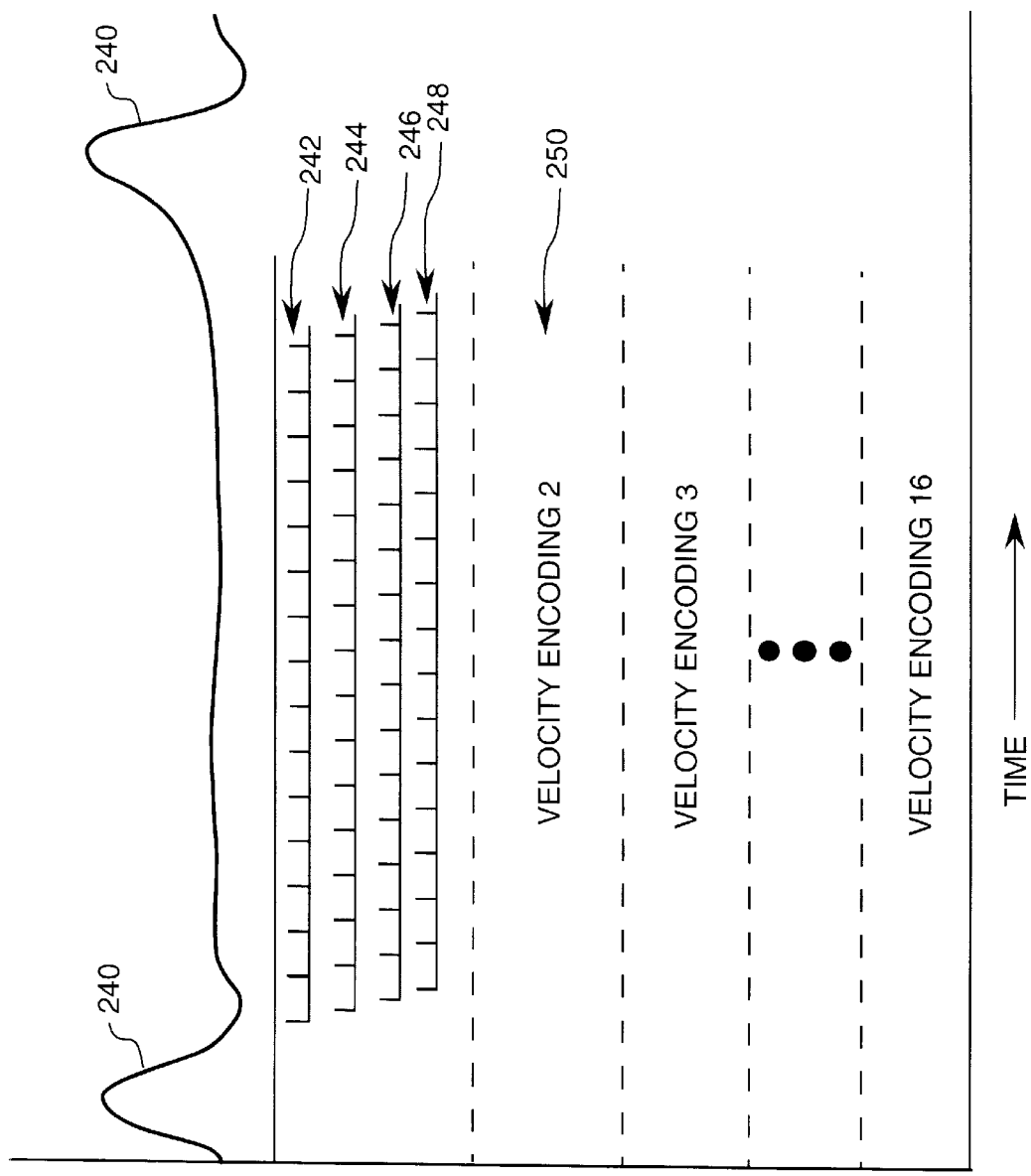
FIG. 4 is a graphic representation of a segmented, cardiac gated method for acquiring the NMR data.

As indicated in FIG. 4, acquisitions are triggered at a preset time after a cardiac trigger signal 240 in the ECG signal is detected. During the first cardiac cycle the sixteen acquisitions 242 are begun 1 ms after the trigger signal 240, and a first velocity encoding value is used throughout. During the next three cardiac cycles sixteen acquisitions 244, 246 and 248 occur at the same velocity encoding, but the start times are delayed by 6 ms, 12 ms and 18 ms respectively, relative to acquisition 242. As a result, a total of 64 acquisitions at 6 ms intervals during the cardiac cycle are made at the first velocity encoding. The same sequence is repeated with a second velocity encoding value 250. Again, 64 acquisitions at 6 ms intervals are made, sorted according to acquisition time, and stored. This process is repeated for 16 different velocity encoding values. With a bipolar velocity encoding gradient 208 (FIG. 2) peak amplitude of 1 G/cm and a duration for each lobe of 4.3 ms, a velocity resolution of 10 cm/s is achieved. This is sufficient to accurately track the moving velocity wave.

The acquired NMR data for each velocity image frame is a data set comprised of sixteen velocity encoded NMR signals sampled in the presence of readout gradient pulse 212 (FIG. 2). This acquired data set is Fourier transformed, first along the readout axis to locate signals along longitudinal axis 200 (FIG. 3), and along the velocity encoding axis to indicate the distribution of spin velocities at the different locations along longitudinal axis 200.

Figure 5:
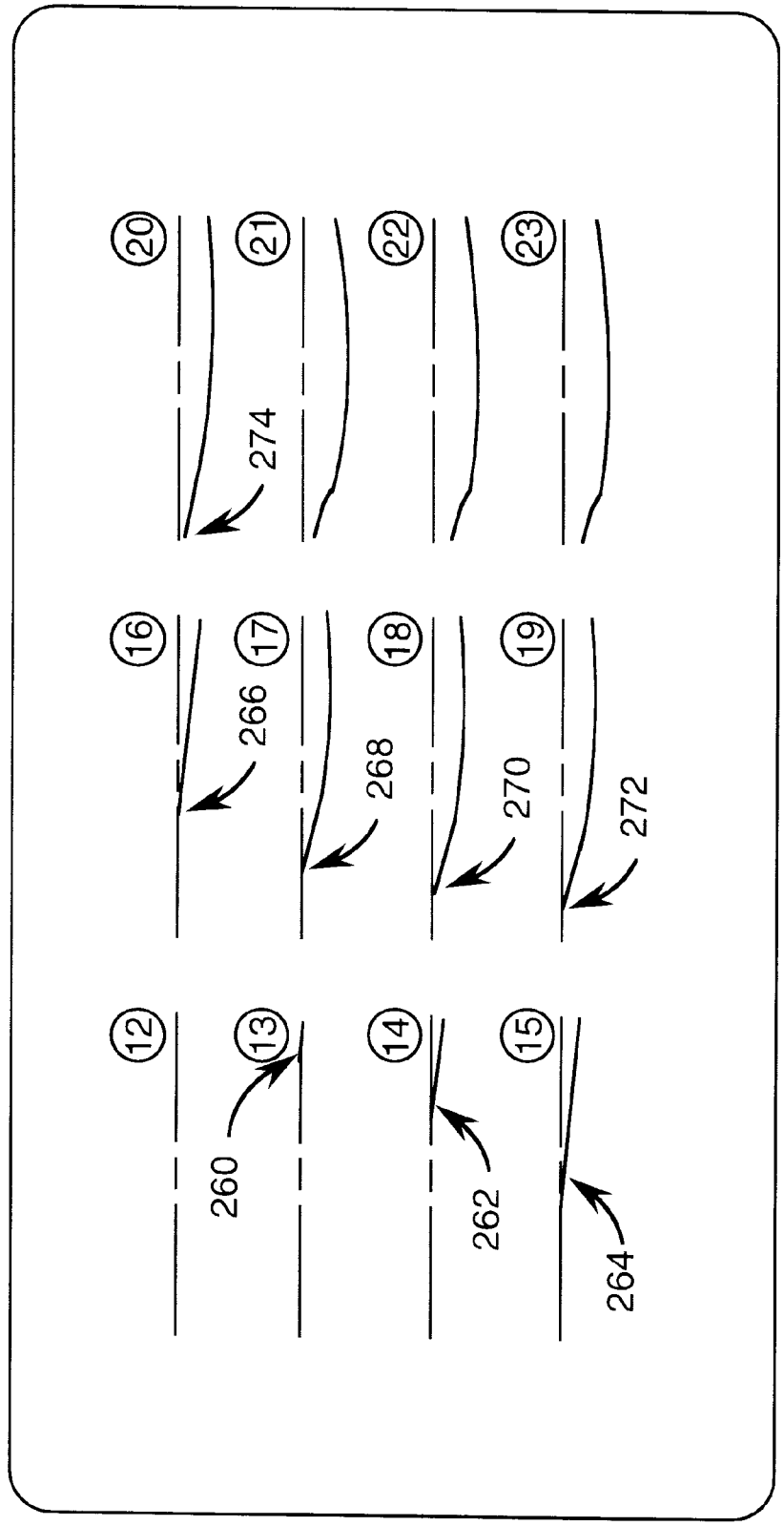
FIG. 5 is a pictorial representation of velocity image frames reconstructed from the acquired NMR data.

Twelve exemplary velocity image frames are shown in FIG. 5. The horizontal direction indicates location x along longitudinal axis 200 (FIG. 3) and the vertical direction indicates velocity v. The intensity of the signal at some point (x,v) in the jth frame can be represented as I(x,v,j). The base horizontal line in each image frame is the signal produced by stationary spins in the field of view of the excited cylindrical volume. Although 64 image frames are acquired during the scan, only frame numbers 12 through 23 are displayed in FIG. 5 because they depict the velocity wave movement through the field of view. More specifically, the propagating wavefront first appears at location 260 in frame 13 and at locations 262–274 in the subsequent image frames 14–20. This velocity wave moves from right to left through the field of view and produces a characteristic feature in the velocity image which reveals its location. Since the image frames are "snapshots" at known time intervals (e.g. 6 ms), the velocity C of the velocity wave can be calculated by determining the distance that this characteristic feature moves from frame to frame.

Figure 6:
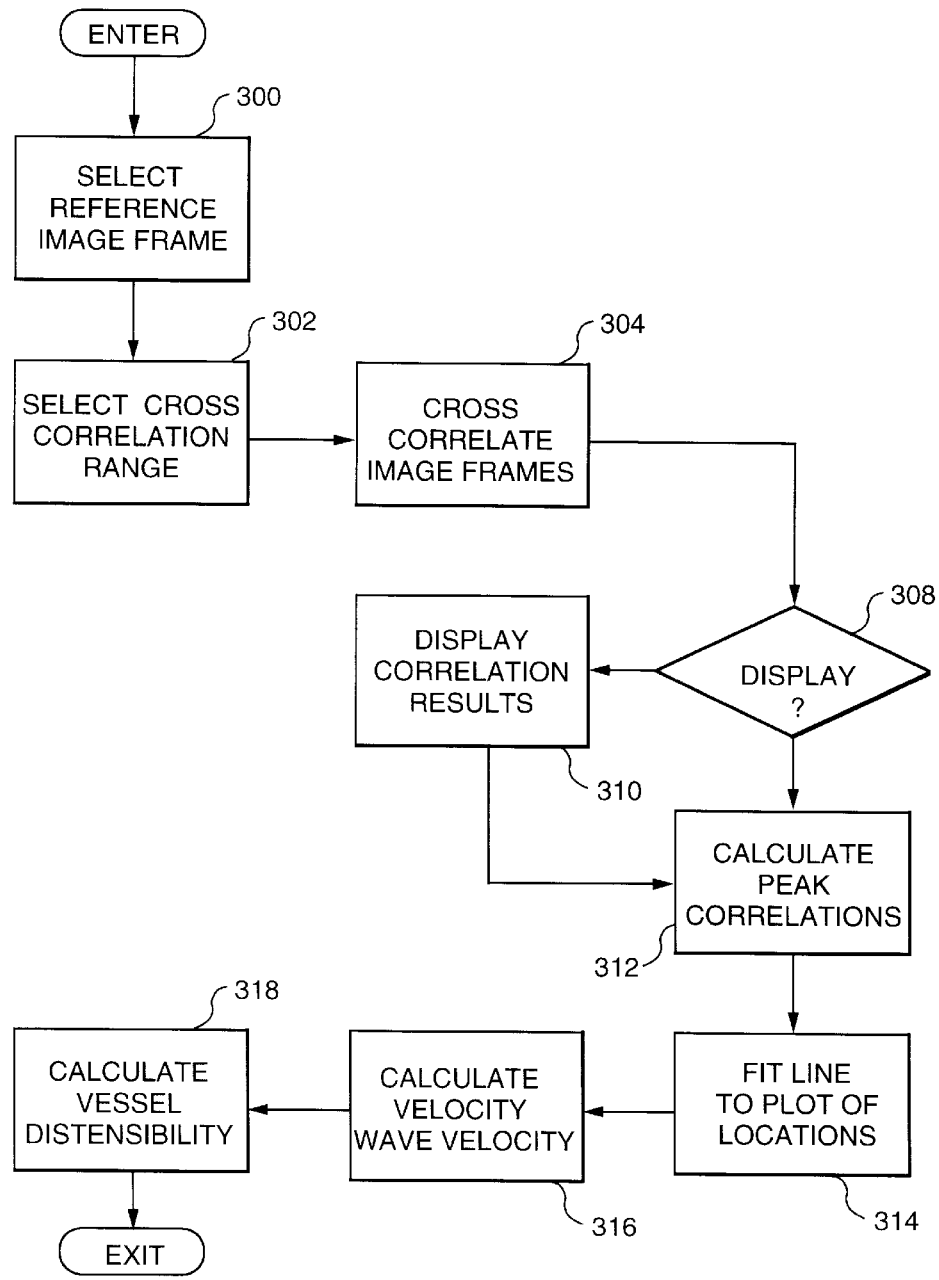
FIG. 6 is a flow chart of the method used to calculate wave velocity from the acquired NMR data.

Calculation of the propagation velocity of the velocity wave, depicted in a series of image frames, is performed by a program executed by computer system 107 (FIG. 1) and depicted by the flow chart of FIG. 6. The first step 300 in the process of executing the program is to select one of the image frames as a reference R. The image frames are displayed and the user selects one reference frame jref in which the pressure wave is clearly visible. For example, the user might select, as a reference frame, frame jref=16 in the series of frame images shown in FIG. 5. In this case R(x,v)=I(x,v,j=jref=16). As the next process step 302, the user selects the range over which this reference image frame is to be cross correlated. The image frames over this range are those which depict the velocity wave traversing the field of view, and in the example shown in FIG. 5, this range may encompass frames 13 through 20.

As indicated at process step 304, the reference image frame is then cross correlated with each of the other image frames j in the selected range to yield a cross-correlation function XC(x,j). The cross correlation is performed in a manner similar to that described in Ronald N. Bracewell, The Fourier Transform and its Applications, McGraw-Hill, New York, Second Edition, 1978, p. 46. Thus, for each frame j in the selected range, $$XC(x, j) = \sum_{u=-umax}^{umax} \sum_{v=-vmax}^{vmax} R(u - x, v)I(u, v, j) \qquad \text{Eq. 3}$$

where u=-umax represents the extreme left of the image, u=umax is the extreme right, v=-vmax is the bottom, and v=vmax is the top. When j=jref in Eq. 3, then I(u,v,j)=R(u,v), and Eq. 3 becomes an autocorrelation. The maximum of this function is located at x=0. This is the same as the cross correlation process except the correlation is performed by moving one copy of the reference image and correlating it with another stationary copy of the reference image.

The result of cross correlation step 304 is a series of correlation values which indicate the degree of correlation as a function of position along longitudinal axis 200 (FIG. 3). The user may elect to display these correlation functions at decision step 308 and produce a suitable display at process step 310.

The location of the velocity wave in each image frame is calculated by locating the peak value of the correlation function in each frame, as indicated at process step 312. This may be as simple as comparing correlation values and picking the location of the highest correlation value. The locations of these peak values in successive image frames are then plotted as a function of time and a straight line is fit to the resulting plot, as indicated at process step 314. A least-squares method for making the best fit is used, as described in W. H. Press, B. P. Flannery, S. A. Teukolsky, and W. T. Vetterling, Numerical Recipes, Cambridge University Press, Cambridge, 1986, p. 499ff. The propagation of the velocity wave is then calculated, as indicated at process step 316, by determining the slope of this line; that is, the change in peak correlation location as a function of time is a measure of the velocity wave propagation velocity. The final process step 318 is to calculate the distensibility of the blood vessel as described above.

A number of measures can be taken to make this automatic determination of wave velocity more robust. First, since the central, zero-velocity baseline in the image frames (FIG. 5) contributes a large portion of the signal to the cross-correlation function without contributing information about the location of the moving pressure wave, these baseline data are zeroed before performing cross correlation step 304 (FIG. 6). Also, rather than using the reconstructed image frames directly, the images may be filtered to remove ghosts and other artifacts. In the preferred embodiment this is accomplished by calculating the normalized square of each image frame pixel value. This has the effect of emphasizing the high-intensity pixels at the expense of the low-to-moderate intensity pixels, thus suppressing artifacts relative to the main velocity trace.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A method for measuring pressure wave velocity in a blood vessel, comprising the steps of:
   a) acquiring a series of image frames from an MRI system which depicts movement of a velocity wave along the blood vessel at a succession of time intervals;
   b) selecting one of the image frames as a reference image;
   c) cross correlating the reference image with selected others of the image frames to determine the relative positions of features therein that indicate velocity wave location; and d) calculating propagation velocity of the velocity wave from the relative positions determined in step c).

2. The method of claim 1 wherein step d) is performed by fitting a line to a plot of said relative positions and calculating wave velocity from the slope of this line.

3. The method of claim 1 wherein each of the cross correlations of the reference image and the selected others of the image frames exhibits a respective peak and step c) is performed by finding the respective peak in the cross correlation of the reference image and each of the selected other image frames.

4. The method of claim 1 including the step of Fourier transforming the image frames acquired in step a) so as to indicate distribution of spin velocities in a field of view which includes the blood vessel.

5. The method of claim 4 including the step of filtering the acquired image frames to suppress artifacts before performing step c).

6. The method of claim 5 wherein the filtering step comprises the step of calculating a normalized square of each pixel value in the image frames.

7. The method of claim 4 including, before performing step c), the step of setting to substantially zero value pixel values in the acquired image frames that indicate substantially zero wave velocity.

* * * * *